United States Patent
Gold et al.

(10) Patent No.: US 10,549,347 B2
(45) Date of Patent: Feb. 4, 2020

(54) SYSTEM AND METHOD FOR AUTHENTICATING COMPONENTS

(71) Applicant: General Electric Company, Schenectady, NY (US)

(72) Inventors: Scott Alan Gold, Waynesville, OH (US); Justin Mamrak, Loveland, OH (US)

(73) Assignee: General Electric Company, Schenectady, NY (US)

( * ) Notice: Subject to any disclaimer, the term of this patent is extended or adjusted under 35 U.S.C. 154(b) by 260 days.

(21) Appl. No.: 15/479,413

(22) Filed: Apr. 5, 2017

(65) Prior Publication Data

US 2018/0292337 A1  Oct. 11, 2018

(51) Int. Cl.
| | |
|---|---|
| *B22F 3/105* | (2006.01) |
| *B33Y 80/00* | (2015.01) |
| *B33Y 50/02* | (2015.01) |
| *B33Y 10/00* | (2015.01) |

(52) U.S. Cl.
CPC ............ *B22F 3/1055* (2013.01); *B33Y 10/00* (2014.12); *B33Y 50/02* (2014.12); *B33Y 80/00* (2014.12); *B22F 2003/1057* (2013.01)

(58) Field of Classification Search
CPC .. G01N 29/04; G01N 29/043; G01N 29/2418; G01N 29/26; G01N 29/4427; G01N 2291/2693; C23C 16/042; B33Y 50/02; B33Y 10/00; C21D 10/005; C22F 3/00; B22F 2003/1057; B22F 2998/10; B22F 3/1055
See application file for complete search history.

(56) References Cited

U.S. PATENT DOCUMENTS

| | | | |
|---|---|---|---|
| 4,350,883 A | 9/1982 | Lagarde | |
| 4,806,740 A | 2/1989 | Gold et al. | |
| 5,182,513 A * | 1/1993 | Young | G01N 27/904 324/232 |
| 5,313,193 A | 5/1994 | Dubois et al. | |
| 5,546,462 A | 8/1996 | Indeck et al. | |
| 6,337,122 B1 | 1/2002 | Grigg et al. | |
| 6,640,632 B1 | 11/2003 | Hatanaka et al. | |
| 6,850,592 B2 | 2/2005 | Schramm et al. | |

(Continued)

FOREIGN PATENT DOCUMENTS

WO   WO2016/109111 A1   7/2016

OTHER PUBLICATIONS

I Gibson, D.W. Rosen and B. Stucker (2010): Additive Manufacturing Technologies, Springer (Year: 2010).*

*Primary Examiner* — Jessee R Roe
*Assistant Examiner* — Rebecca Janssen
(74) *Attorney, Agent, or Firm* — Dority & Manning, P.A.

(57) ABSTRACT

A system and method for manufacturing and authenticating a component is provided. The method includes forming a component having an identifying region that contains two or more materials having different conductivities such that the identifying region generates an eddy current response signature that defines a component identifier of the component. The method further includes interrogating the identifying region of the surface with an eddy current probe to determine the component identifier. The component identifier may be stored in a database as a reference identifier and may be used for authenticating components.

18 Claims, 6 Drawing Sheets

(56) References Cited

U.S. PATENT DOCUMENTS

| | | |
|---|---|---|
| 6,976,627 B1 | 12/2005 | Culp et al. |
| 7,148,448 B2 | 12/2006 | Warren, Jr. et al. |
| 7,199,367 B2 | 4/2007 | Favro et al. |
| 7,217,102 B2 | 5/2007 | Rockstroh et al. |
| 7,250,864 B2 | 7/2007 | Murofushi et al. |
| 7,584,833 B2 | 9/2009 | Howells |
| 7,602,963 B2 | 10/2009 | Nightingale et al. |
| 8,222,567 B2 | 7/2012 | Mathai et al. |
| 8,536,860 B2 | 9/2013 | Boenisch |
| 8,837,672 B2 | 9/2014 | Nance et al. |
| 8,935,286 B1 | 1/2015 | Westerman, Jr. et al. |
| 8,973,829 B2 | 3/2015 | Atkinson et al. |
| 8,985,471 B2 | 3/2015 | Freeman |
| 9,036,916 B2 | 5/2015 | Le |
| 9,074,927 B2 | 7/2015 | Singh et al. |
| 9,250,183 B2 | 2/2016 | Smith et al. |
| 9,311,652 B2 | 4/2016 | Farn et al. |
| 9,360,589 B1 * | 6/2016 | Meinhold ............ G01N 21/643 |
| 9,400,910 B2 | 7/2016 | Kumar et al. |
| 9,414,891 B2 | 8/2016 | Kieser |
| 9,424,503 B2 | 8/2016 | Kieser |
| 2002/0126889 A1 | 9/2002 | Pikler et al. |
| 2008/0159529 A1 | 7/2008 | Aarts et al. |
| 2009/0286007 A1 | 11/2009 | Brancher |
| 2013/0193214 A1 | 8/2013 | Margulis et al. |
| 2014/0205083 A1 | 7/2014 | Pryakhin et al. |
| 2014/0263674 A1 | 9/2014 | Cerveny |
| 2015/0147585 A1 | 5/2015 | Schwarze et al. |
| 2015/0308337 A1 | 10/2015 | Marasco et al. |
| 2015/0324677 A1 | 11/2015 | Talyansky et al. |
| 2016/0107764 A1 | 4/2016 | O'Kell et al. |
| 2016/0207345 A1 | 7/2016 | Farmer et al. |
| 2016/0253586 A1 | 9/2016 | Cook et al. |
| 2016/0260001 A1 | 9/2016 | Flores et al. |
| 2016/0283834 A1 | 9/2016 | Bobbitt, III |
| 2016/0298268 A1 | 10/2016 | Gallucci et al. |
| 2016/0306088 A1 | 10/2016 | Ouderkirk et al. |
| 2016/0307083 A1 | 10/2016 | Kumar et al. |
| 2016/0311164 A1 | 10/2016 | Miyano |
| 2017/0120338 A1 | 5/2017 | Goeing et al. |
| 2017/0232779 A1 | 8/2017 | Viens et al. |

* cited by examiner

SYSTEM AND METHOD FOR AUTHENTICATING COMPONENTS

FIELD

The present subject matter relates generally to additively manufactured components, and more particularly, to systems and methods for authenticating additively manufactured components including features for improved part identification or counterfeit prevention.

BACKGROUND

Original equipment manufacturers (OEMs) in a variety of industries have an interest in ensuring that replacement components used with their products or equipment are manufactured according to standards set and controlled by the OEM. Using the aviation industry as an example, the manufacturer of a gas turbine engine, as well as the airlines and the passengers that rely on them, can be exposed to serious risks if counterfeit or replica replacement parts are readily available for and installed on these engines.

For example, such counterfeit components can pose a severe risk to the integrity of the gas turbine engines or may otherwise result in a variety of problems for the OEM and the end user. More specifically, OEM components may require rigorous attention to detail to ensure sound material properties and capabilities for the specific application as well as sophisticated inspections to verify the component performance. OEMs cannot ensure the integrity or compatibility of counterfeit parts, which may result in dangerous engine operation and increase the risk of potential failure.

In addition, counterfeit parts compromise the OEMs ability to control the quality associated with their products. For example, inexpensive replicas and inferior components on the market are a real threat, both to the engines on which they are installed and to the reputation of the OEM. Moreover, failure of a gas turbine engine due to a counterfeit replacement component might subject the OEM to misdirected legal liability and OEMs may lose a significant revenue stream by not being able to control the sale of OEM replacement components.

Additive manufacturing technologies are maturing at a fast pace. For example, very accurate additive manufacturing printers using a variety of materials, such as metals and polymers, are becoming available at decreasing costs. In addition, improved scanning technologies and modeling tools are now available. As a result, certain OEMs are beginning to use such technologies to produce original and replacement parts. However, the advance of additive manufacturing technologies also results in a lower barrier to entry into the additive manufacturing space. Therefore, replacement components may be more easily reverse engineered and copied, and there is an increased risk of third parties manufacturing and installing counterfeit components on OEM equipment, such as a gas turbine engine, resulting in the dangers described briefly above.

There is thus a need for a technology that allows genuine parts to be distinguished from counterfeits to ensure that parts created through additive manufacturing cannot be duplicated by an unauthorized third party and passed off as genuine OEM parts. Accordingly, systems and methods for authenticating additively manufactured components to distinguish genuine parts from counterfeit parts would be useful.

BRIEF DESCRIPTION

Aspects and advantages of the invention will be set forth in part in the following description, or may be obvious from the description, or may be learned through practice of the invention.

In one exemplary embodiment of the present disclosure, a method for manufacturing a component is provided. The method includes forming a cross sectional layer having a surface, the cross sectional layer including a conductivity modifying agent. The method further includes obtaining data indicative of a component identifier by interrogating an identifying region of the surface with an eddy current probe, wherein the conductivity modifying agent is selectively positioned within the identifying region of the surface such that the interrogation of the identifying region results in an eddy current response signature that defines the component identifier of the component. The component identifier is stored in a database as a reference identifier.

In another exemplary aspect of the present disclosure, a method of authenticating a component is provided. The method includes locating an identifying region of the component, the identifying region including a first material having a first conductivity and a second material having a second conductivity, the second material being selectively positioned within the first material such that the identifying region generates an eddy current response signature that defines a component identifier of the component. The method further includes obtaining data indicative of the component identifier of the component by interrogating the identifying region of the surface of the component using an eddy current probe and determining, by one or more processors, that the component is authentic based on the data acquired by the eddy current probe.

In still another exemplary aspect of the present disclosure, a system for authenticating an additively manufactured component is provided. The system includes one or more processors and one or more memory devices, the one or more memory devices storing computer-readable instructions that when executed by the one or more processors cause the one or more processors to perform operations. The operations include obtaining data indicative of an identifying region on the component, the identifying region including a first material having a first conductivity and a second material having a second conductivity, the second material being selectively positioned within the first material such that the identifying region generates an eddy current response signature that defines a component identifier of the component. The operations further includes determining the component identifier by interrogating the identifying region of the component using an eddy current probe, obtaining a reference identifier from a database, and determining that the component is authentic if the component identifier matches the reference identifier.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

FIG. 1 provides a perspective view of an additively manufactured component according to an exemplary embodiment of the present subject matter.

Repeat use of reference characters in the present specification and drawings is intended to represent the same or analogous features or elements of the present invention.

DETAILED DESCRIPTION

Reference will now be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention.

The present disclosure is generally directed to a system and method for manufacturing and authenticating a component. The method includes forming a component having an identifying region that contains two or more materials having different conductivities such that the identifying region generates an eddy current response signature that defines a component identifier of the component. The method further includes interrogating the identifying region of the surface with an eddy current probe to determine the component identifier. The component identifier may be stored in a database as a reference identifier and may be used for authenticating components.

In general, the components described herein may be manufactured or formed using any suitable process. However, in accordance with several aspects of the present subject matter, these components may be formed using an additive-manufacturing process, such as a 3-D printing process. The use of such a process may allow the components to be formed integrally, as a single monolithic component, or as any suitable number of sub-components. In particular, the manufacturing process may allow these components to be integrally formed and include a variety of features not possible when using prior manufacturing methods. For example, the additive manufacturing methods described herein enable the manufacture of components having various features, configurations, thicknesses, materials, densities, surface variations, and identifying features not possible using prior manufacturing methods. Some of these novel features are described herein.

As used herein, the terms "additively manufactured" or "additive manufacturing techniques or processes" refer generally to manufacturing processes wherein successive layers of material(s) are provided on each other to "build-up," layer-by-layer, a three-dimensional component. The successive layers generally fuse together to form a monolithic component which may have a variety of integral sub-components. Although additive manufacturing technology is described herein as enabling fabrication of complex objects by building objects point-by-point, layer-by-layer, typically in a vertical direction, other methods of fabrication are possible and within the scope of the present subject matter. For example, although the discussion herein refers to the addition of material to form successive layers, one skilled in the art will appreciate that the methods and structures disclosed herein may be practiced with any additive manufacturing technique or manufacturing technology. For example, embodiments of the present invention may use layer-additive processes, layer-subtractive processes, or hybrid processes.

Suitable additive manufacturing techniques in accordance with the present disclosure include, for example, Fused Deposition Modeling (FDM), Selective Laser Sintering (SLS), 3D printing such as by inkjets and laserjets, Stereolithography (SLA), Direct Selective Laser Sintering (DSLS), Electron Beam Sintering (EBS), Electron Beam Melting (EBM), Laser Engineered Net Shaping (LENS), Laser Net Shape Manufacturing (LNSM), Direct Metal Deposition (DMD), Digital Light Processing (DLP), Direct Selective Laser Melting (DSLM), Selective Laser Melting (SLM), Direct Metal Laser Melting (DMLM), and other known processes.

The additive manufacturing processes described herein may be used for forming components using any suitable material. For example, the material may be plastic, metal, concrete, ceramic, polymer, epoxy, photopolymer resin, or any other suitable material that may be in solid, liquid, powder, sheet material, wire, or any other suitable form. More specifically, according to exemplary embodiments of the present subject matter, the additively manufactured components described herein may be formed in part, in whole, or in some combination of materials including but not limited to pure metals, nickel alloys, chrome alloys, titanium, titanium alloys, magnesium, magnesium alloys, aluminum, aluminum alloys, and nickel or cobalt based superalloys (e.g., those available under the name Inconel® available from Special Metals Corporation). These materials are examples of materials suitable for use in the additive manufacturing processes described herein, and may be generally referred to as "additive materials."

In addition, one skilled in the art will appreciate that a variety of materials and methods for bonding those materials may be used and are contemplated as within the scope of the present disclosure. As used herein, references to "fusing" may refer to any suitable process for creating a bonded layer of any of the above materials. For example, if an object is made from polymer, fusing may refer to creating a thermoset bond between polymer materials. If the object is epoxy, the bond may be formed by a crosslinking process. If the material is ceramic, the bond may be formed by a sintering process. If the material is powdered metal, the bond may be formed by a melting or sintering process. One skilled in the art will appreciate that other methods of fusing materials to make a component by additive manufacturing are possible, and the presently disclosed subject matter may be practiced with those methods.

In addition, the additive manufacturing process disclosed herein allows a single component to be formed from multiple materials. Thus, the components described herein may be formed from any suitable mixtures of the above materials. For example, a component may include multiple layers, segments, or parts that are formed using different materials, processes, and/or on different additive manufacturing machines. In this manner, components may be constructed which have different materials and material properties for meeting the demands of any particular application. In addition, although the components described herein are constructed entirely by additive manufacturing processes, it should be appreciated that in alternate embodiments, all or a portion of these components may be formed via casting, machining, and/or any other suitable manufacturing process. Indeed, any suitable combination of materials and manufacturing methods may be used to form these components.

An exemplary additive manufacturing process will now be described. Additive manufacturing processes fabricate components using three-dimensional (3D) information, for example a three-dimensional computer model, of the component. Accordingly, a three-dimensional design model of the component may be defined prior to manufacturing. In this regard, a model or prototype of the component may be scanned to determine the three-dimensional information of the component. As another example, a model of the component may be constructed using a suitable computer aided design (CAD) program to define the three-dimensional design model of the component.

The design model may include 3D numeric coordinates of the entire configuration of the component including both external and internal surfaces of the component. For example, the design model may define the body, the surface, and/or any surface features such as irregularities, component identifiers, localized material variations, or datum features, as well as internal passageways, openings, support structures, etc. In one exemplary embodiment, the three-dimensional design model is converted into a plurality of slices or segments, e.g., along a central (e.g., vertical) axis of the component or any other suitable axis. Each slice may define a thin cross section of the component for a predetermined height of the slice. The plurality of successive cross-sectional slices together form the 3D component. The component is then "built-up" slice-by-slice, or layer-by-layer, until finished.

In this manner, the components described herein may be fabricated using the additive process, or more specifically each layer is successively formed, e.g., by fusing or polymerizing a plastic using laser energy or heat or by sintering or melting metal powder. For example, a particular type of additive manufacturing process may use an energy beam, for example, an electron beam or electromagnetic radiation such as a laser beam, to sinter or melt a powder material. Any suitable laser and laser parameters may be used, including considerations with respect to power, laser beam spot size, and scanning velocity. The build material may be formed by any suitable powder or material selected for enhanced strength, durability, and useful life, particularly at high temperatures.

Each successive layer may be, for example, between about 10 µm and 200 µm, although the thickness may be selected based on any number of parameters and may be any suitable size according to alternative embodiments. Therefore, utilizing the additive formation methods described above, the components described herein may have cross sections as thin as one thickness of an associated powder layer, e.g., 10 µm, utilized during the additive formation process.

In addition, utilizing an additive process, the surface finish and features of the components may vary as need depending on the application. For example, the surface finish may be adjusted (e.g., made smoother or rougher) by selecting appropriate laser scan parameters (e.g., laser power, scan speed, laser focal spot size, overlap between passes, etc.) during the additive process, especially in the periphery of a cross-sectional layer which corresponds to the part surface. For example, a rougher finish may be achieved by increasing laser scan speed or decreasing the size of the melt pool formed, and a smoother finish may be achieved by decreasing laser scan speed or increasing the size of the melt pool formed. The scanning pattern and/or laser power can also be changed to change the surface finish in a selected area.

Notably, in exemplary embodiments, several features of the components described herein were previously not possible due to manufacturing restraints. However, the present inventors have advantageously utilized current advances in additive manufacturing techniques to develop exemplary embodiments of such components generally in accordance with the present disclosure. While the present disclosure is not limited to the use of additive manufacturing to form these components generally, additive manufacturing does provide a variety of manufacturing advantages, including ease of manufacturing, reduced cost, greater accuracy, etc.

In this regard, utilizing additive manufacturing methods, even multi-part components may be formed as a single piece of continuous metal, and may thus include fewer sub-components and/or joints compared to prior designs. The integral formation of these multi-part components through additive manufacturing may advantageously improve the overall assembly process. For example, the integral formation reduces the number of separate parts that must be assembled, thus reducing associated time and overall assembly costs. Additionally, existing issues with, for example, leakage, joint quality between separate parts, and overall performance may advantageously be reduced.

Also, the additive manufacturing methods described above enable much more complex and intricate shapes and contours of the components described herein. For example, such components may include thin additively manufactured layers and novel surface features. All of these features may be relatively complex and intricate for avoiding detection and/or impeding counterfeiting by a third party. In addition, the additive manufacturing process enables the manufacture of a single component having different materials such that different portions of the component may exhibit different performance characteristics. The successive, additive nature of the manufacturing process enables the construction of these novel features. As a result, the components described herein may exhibit improved performance and may be easily distinguished from replicas or counterfeit components.

Figure 1:
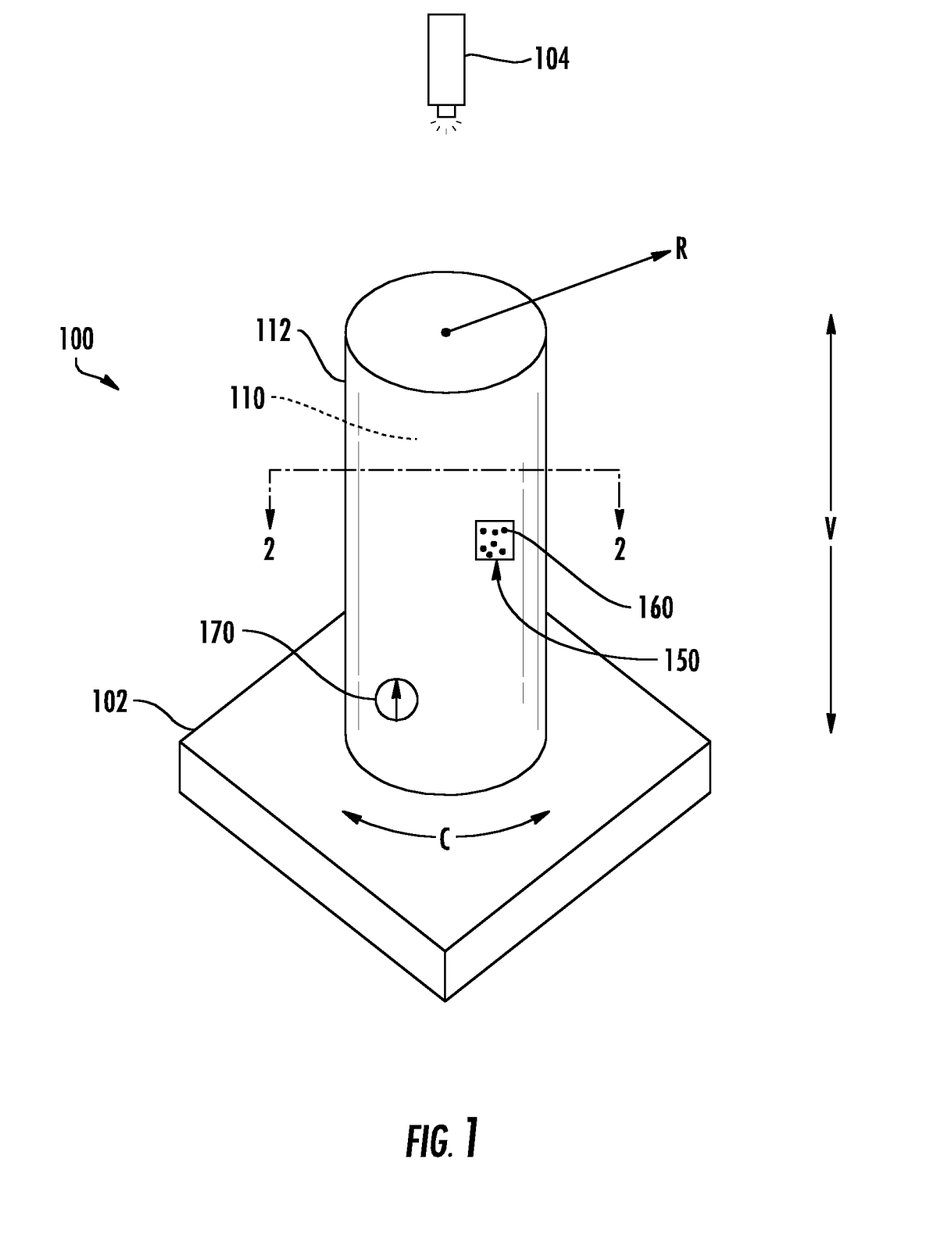
Figure 2:
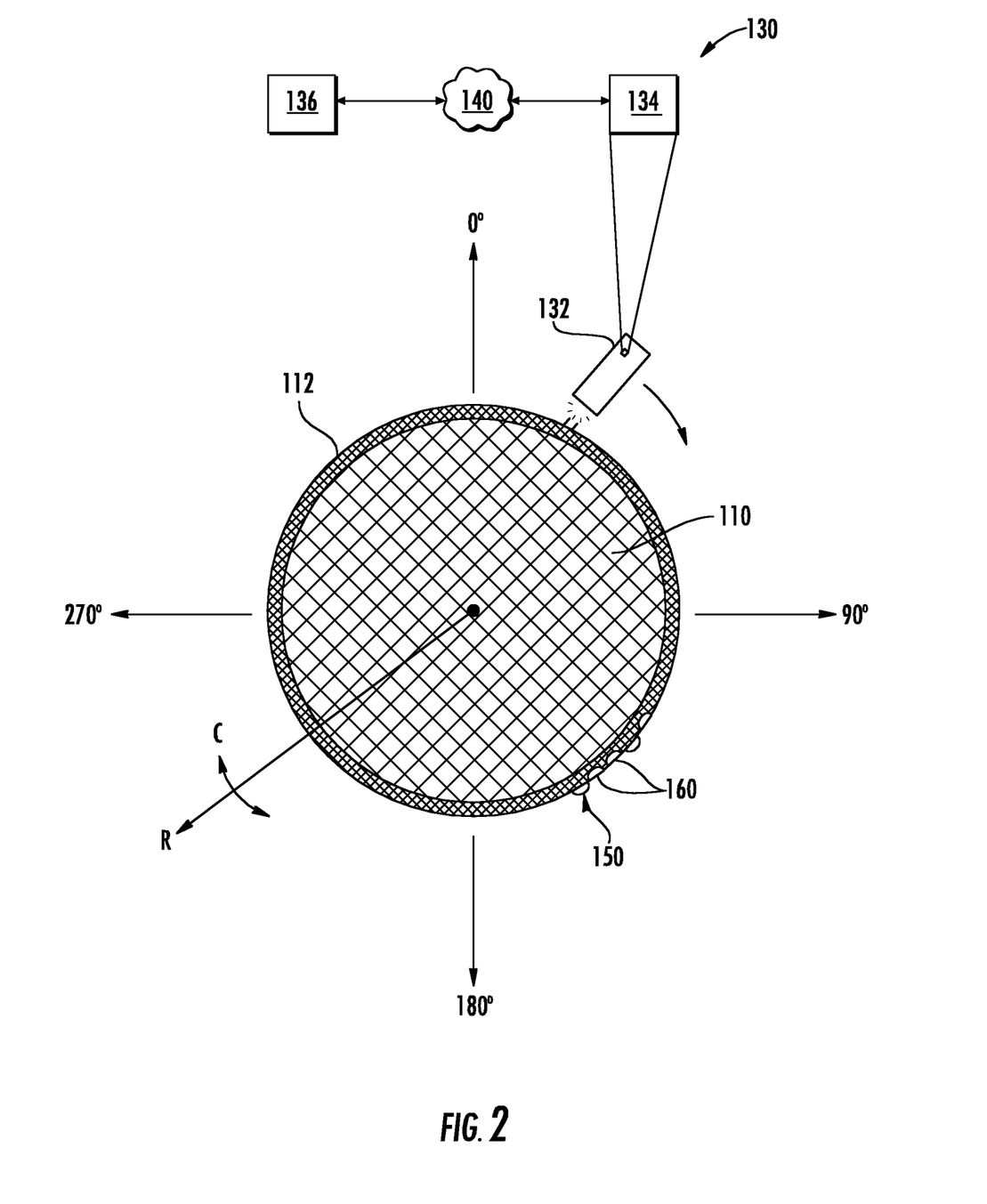
FIG. 2 provides a cross sectional view of the exemplary component of FIG. 1, taken along Line 2-2 of FIG. 1.

Referring now to FIGS. 1 through 2, an additively manufactured component 100 according to an exemplary embodiment of the present subject matter is provided. More specifically, FIG. 1 provides a perspective view of component 100 and FIG. 2 provides a cross sectional view of component 100, taken along Line 2-2 of FIG. 1. For the purpose of explaining aspects of the present subject matter, component 100 is a simple, solid cylinder. However, it should be appreciated that the additive manufacturing methods described herein may be used to form any suitable component for any suitable device, regardless of its material or complexity. As illustrated, component 100 generally defines a radial direction R, a circumferential direction C, and a vertical direction V.

Also illustrated in FIG. 1 is an additive manufacturing platform 102 and an energy source 104, as may be used according to any of the additive manufacturing methods described above. For example, component 100 may be constructed by laying a powder bed onto platform 102 and selectively fusing the powder bed at desired locations using energy source 104 to form a layer of component 100. Platform 102 may be lowered along the vertical direction V after each layer is formed and the process may be repeated until component 100 is complete.

Referring to FIG. 2, a cross sectional view of component 100 taken along Line 2-2 (or more specifically, a plane corresponding to this line) will be described. It should be appreciated that FIG. 2 illustrates a top view of a single additively manufactured layer of component 100 having a finite thickness. As illustrated, component 100 includes a cross sectional layer 110. Cross sectional layer 110 may generally define an interior body layer and a surface 112. As used herein, "interior body layer" may refer to any structure, body, surface, base layer, or other portion of component 100 on which a surface may be formed. In this regard, for example, component 100 includes surface 112 that is formed around cross sectional layer 110, i.e., along a perimeter or periphery of cross sectional layer 110 along the circumferential direction C. As used herein, "surface" may refer to the periphery of one or more cross sectional layer 110 of component 100, e.g., formed on an otherwise exposed interior body layer.

According to the illustrated embodiment, cross sectional layer 110 and surface 112 may be formed at different energy levels and may have different structural characteristics. As used herein, an "energy level" of an energy source is used generally to refer to the magnitude of energy the energy source delivers to a particular point or region of component 100. For example, if the energy source is a laser or an electron beam, the energy level is generally a function of the power level and the scan speed of the laser or electron beam. As used herein, "scan speed" is used generally to refer to the linear velocity of the energy source along a surface of the additively manufactured component. Notably, the energy level of an energy source directed toward a powder bed may also be manipulated by adjusting the scanning strategy, e.g., by increasing the overlap between adjacent passes of the energy source over the powder bed.

Adjusting the energy level of energy source 104 can enable the formation of component 100 with different regions having different densities and structural properties. For example, a higher energy level may be achieved by increasing the power level of energy source 104 (e.g., in Watts), decreasing its scan speed, or increasing the overlap between adjacent passes of energy source 104 to direct more energy onto a single area of the powder bed. By contrast, a lower energy level may be achieved by decreasing the power level of energy source 104, increasing its scan speed, or decreasing the overlap between adjacent passes of energy source 104 to direct less energy onto a single area of the powder bed.

According to the exemplary embodiment, component 100 is formed by moving energy source 104 (or more specifically, a focal point of the energy source 104, as shown in FIG. 1) along a powder bed placed on platform 102 to fuse together material to form component 100. According to the exemplary embodiment, a first energy level (e.g., a higher energy level) is used to form cross sectional layer 110 and a second energy level (e.g., a lower energy level) is used to form surface 112. It should be appreciated that this is only one exemplary construction of component 100. According to alternative embodiments, components formed using the methods described herein may have any suitable size and number of sections formed using any suitable energy source, at any suitable energy level, and having any suitable scanning strategy.

According to exemplary embodiments of the present subject matter, component 100 may include a component identifier that may be used by the component manufacturer, an end user, or another third party to authenticate or positively identify component 100. For example, the component identifier may be integrated with component 100 such that the component identifier remains associated with component 100 throughout the lifetime of component 100. The component identifier may be unique to a specific component, may be associated with a group of components manufactured at the same time, or may refer to a type of component in general.

Exemplary component identifiers may be any sequence of features such as bumps, divots, or other surface aberrations that contain or define encoded information in a manner analogous to a printed serial number, a bar code, or a QR code, e.g., for uniquely identifying component 100. In addition, such component identifiers may be localized component materials, configurations, densities, surface variations, or other features suitable for generating the component identifier when interrogated with some type of scanner, such as described below. The component identifiers may be inherent in the manufactured component (e.g., a pattern of surface roughness) or may be intentionally designed and manufactured into the component. The exemplary component identifiers described herein are used only to illustrate aspects of the present subject matter and are not intended to limit its scope.

In order to read the component identifiers to identify, distinguish, or authenticate component 100, the manufacturer or an authorized end user may use some suitable scanning device, probe, or detector for reading the component identifier. For example, referring to FIG. 2 an authentication system 130 for authenticating components will be described according to exemplary embodiments of the present subject matter. Authentication system 130 may generally include an eddy current probe 132 for measuring the eddy current response of one or more locations on surface 112 of component 100.

According to the illustrated embodiment, eddy current probe 132 is generally configured for using principles of electromagnetic induction to induce eddy currents in component 100 and measuring the eddy current response, as described below. This process of inducing eddy currents and reading, mapping, or otherwise obtaining useful data regarding the eddy current response signature of component 100 is referred to herein as "interrogation" of component 100. Eddy current probe 132 may pass over surface 112 of component 100 in any suitable manner for interrogating surface 112, or otherwise rendering some useful data regarding surface 112 of component 100, e.g., the component identifier.

In this regard, for example, eddy current probe 132 may be any device suitable for interrogating component 100 using principles of electromagnetic induction. In general, eddy current probe 132 may have at least one wire coil through which an alternating current flows, thereby generating an oscillating magnetic field. When a conductive material is positioned within the oscillating magnetic field, a circular flow of electrons known as an eddy current will begin to move through the conductive material, generating its own magnetic field. The magnetic fields in the coil and the conductive material interact in a manner that can be detected by eddy current probe 132 as a unique eddy current response signature.

Notably, the eddy current response signature may vary depending on a variety of factors associated with component 100. For example, the conductivity or conductivities of materials in the interrogation region, material densities, the surface roughness, microscopic cracks in surface 112, and other component 100 features may affect the eddy current response signature. In addition, the eddy current response signature can vary depending on the type of eddy current probe, the number of testing coils, the testing frequencies, the proximity of the probe to the material, and the calibration of a detecting coil. Therefore, different components or even different regions of the same component can generate unique eddy current response signatures that may correspond to a unique component identifier.

According to the illustrated embodiment, eddy current probe 132 includes a controller 134 which is generally configured for receiving, analyzing, transmitting, or otherwise utilizing data acquired by eddy current probe 132. Controller 134 can include various computing device(s) (e.g., including processors, memory devices, etc.) for performing operations and functions, as described herein. For reasons described in more detail below, eddy current probe 132, or more specifically, controller 134, may further be in communication with a database or remote computing system 136, e.g., via a network 140, and may be configured for transmitting or receiving information related to component 100, e.g., such as its component identifier.

Figure 3:
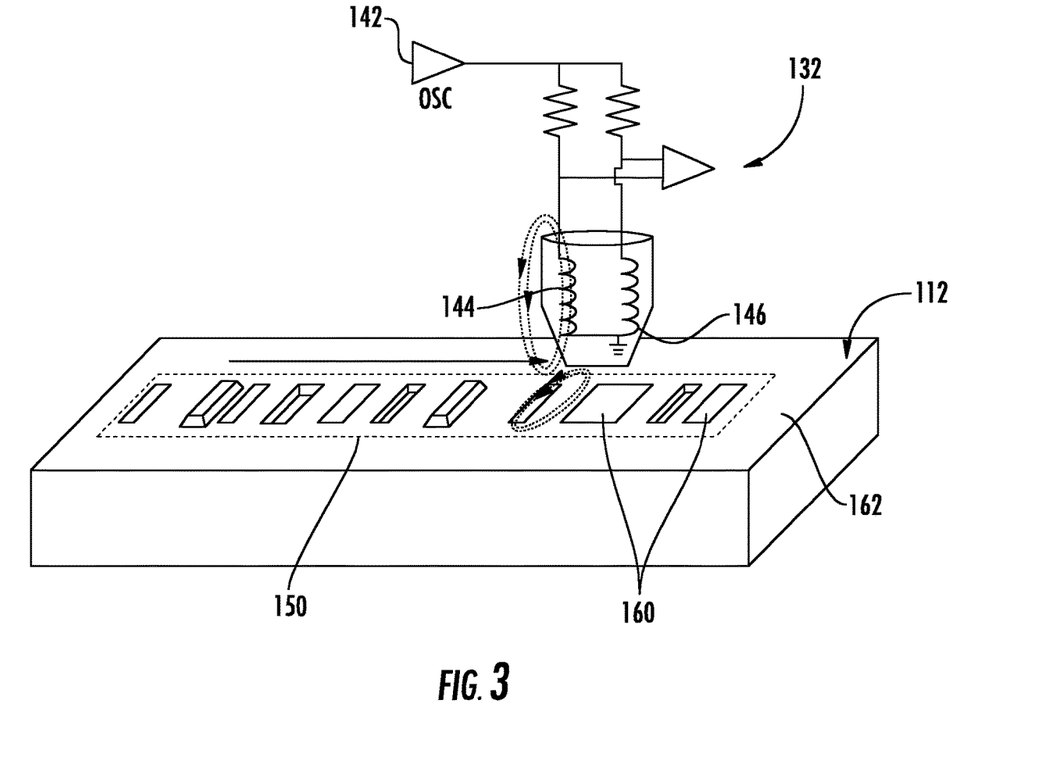
FIG. 3 provides a perspective view of a portion of a surface of the exemplary component of FIG. 1 and an eddy current probe configured for interrogating the surface according to an exemplary embodiment of the present subject matter.

Referring to FIG. 3, a schematic representation of eddy current probe 132 interrogating a surface of a component is illustrated. For example, eddy current probe 132 may be interrogating surface 112 of component 100 to determine the component identifier of component 100. As illustrated, eddy current probe 132 includes an oscillator 142 for generating an alternating current in a magnetic induction coil or test coil 144. To interrogate a component, the test coil 144 is positioned in proximity to the component to generate eddy currents. The eddy current response signature may be detected by a separate coil, illustrated herein as a reference coil 146. According to the illustrated embodiment, test coil 144 and reference coil 146 are bridged together such that the difference between the two signals is output as the eddy current response signature (see, e.g., FIG. 4) from eddy current probe 132.

It should be appreciated that eddy current probe 132 is illustrated herein only for purposes of explaining aspects of the present subject matter. Other probe configurations are possible and within the scope of the present subject matter. For example, eddy current probe 132 may contain any suitable number of induction coils or test coils and may use more than one reference coil to detect the eddy current response at different locations. In addition, eddy current probe 132 may be configured to interrogate component 100 using more than one excitation frequency, either simultaneously using multiple test coils or successively by making multiple passes with the probe at different frequencies. Similarly, other electrical circuit configurations and additional circuit components may be used according to alternative embodiments.

Eddy current probe 132 is generally positioned and oriented for interrogating an identifying region 150 of component 100. In this regard, for example, identifying region 150 may contain a specific structure, material type, pattern, density, or any other suitable features configured for generating a unique eddy current response signature corresponding to the component identifier when interrogated by eddy current probe 132. For example, as illustrated, eddy current probe 132 may travel in a single direction along a length of surface 112 to detect the eddy current response.

A manufacturer of a component may introduce a variety of features to affect the eddy current response and generate a unique component identifier. As explained above, this may be desirable to enable the authentication of genuine manufacturer parts and prevent the use of counterfeit parts. For example, according to the illustrated embodiment, component 100 includes one or more conductivity modifying agents 160 selectively positioned on or within surface 112. As used herein, "conductivity modifying agent" is used to refer to any material or feature that is integrated into component 100 to adjust the localized conductivity, thereby generating a unique response when interrogated by an eddy current probe.

According to the illustrated embodiment, conductivity modifying agents 160 are deposited on surface 112. However, according to alternative embodiments, conductivity modifying agents 160 may be deposited beneath surface 112, e.g., within cross sectional layer 110 or at any other suitable location within component 100. As illustrated, surface 112 contains a primary material 162 and conductivity modifying agents 160 are a second material selectively positioned within surface 112 to generate a unique eddy current response signature. In this regard, for example, primary material 162 may have a first conductivity and conductivity modifying agents 160 may have a second conductivity that is different from the first conductivity. In this manner, by depositing conductivity modifying agents 160 in a unique pattern on surface 112, a unique component identifier may be defined. It should further be appreciated that any suitable number and type of conductivity modifying agents 160 may be used to generate the desired signature. For example, according to alternative exemplary embodiments, identifying region 150 of surface 112 may include two or more conductivity modifying agents 160, e.g., such as a third material having a third conductivity.

Conductivity modifying agents 160 may be formed, for example, by selectively depositing a material, e.g., such as conductivity modifying agents 160, having a different electrical conductivity than portions of the surrounding material. For example, using component 100 as an example, surface 112 may be composed primarily of a primary surface powder having a first electrical conductivity. By selectively positioning a secondary material within the primary surface powder during the additive manufacturing process, a unique eddy current response signature may be achieved when the surface containing the conductivity modifying agents 160 is interrogated using eddy current probe 132.

According to another embodiment, one or more materials may be introduced or otherwise deposited on component 100 using chemical vapor deposition, as is known in the art. An exemplary chemical vapor deposition process may include positioning a shadow mask over surface 112 of component 100. The shadow mask acts as a precise stencil that defines the desired deposit shape and positioning. Volatile precursors containing the desired material may be applied over the shadow mask which only allows deposits in specific areas on surface 112 to deposit the material as desired to generate the component identifier. In this regard, for example, by selectively depositing one or more layers of conductivity modifying agents 160 onto component 100, a unique eddy current response signature may be defined.

Figure 4:
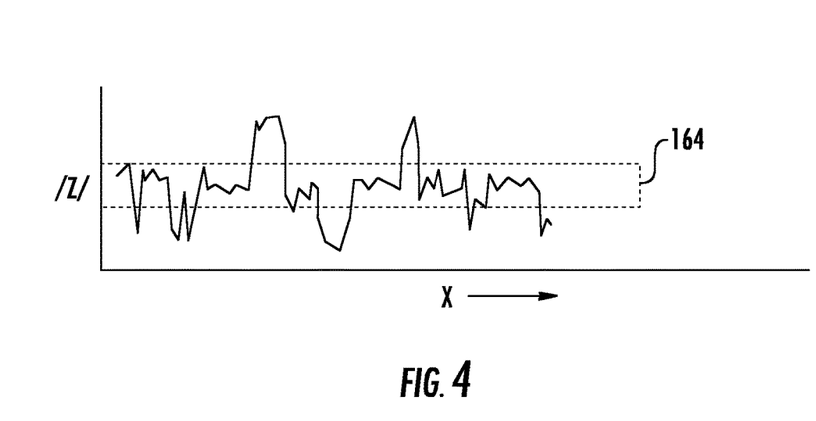
FIG. 4 provides a plot of an eddy current response signature according to an exemplary embodiment of the present subject matter.

FIG. 4 illustrates an eddy current response signature according to an exemplary embodiment of the present subject matter. As illustrated, the response signature is the impedance Z measured by reference coil 146 as eddy current probe 132 travels through identifying region 150 along a single direction X. According to alternative embodiments, eddy current probe can measure a two-dimensional region of surface 112, e.g., as shown in FIG. 1.

Notably, even if surface 112 is formed entirely out of a single material, it will have natural conductivity variations after formation. For example, these variations may be present due to small irregularities introduced to surface 112 during the manufacturing process or due to small variations in material properties, densities, or surface roughness. According to exemplary embodiments, natural conductivity variations may generate their own eddy current response signature which may correspond to a unique component identifier. As shown in FIG. 4, the natural surface variations may generate a signature, i.e., "noise," that is contained within region 164.

According to exemplary embodiments, it may be desirable to differentiate between these inherent variations and conductivity variations introduced by conductivity modifying agents 160. Therefore, conductivity modifying agents 160 may be selected and deposited such that the eddy current response generated by conductivity modifying agents 160 may be distinguished from "noise" generated by the natural surface conductivity variations. In this regard, for example, conductivity modifying agents 160 may have conductivities sufficiently different than primary material 162 to generate an identifiable eddy current response. Controller 134 may be configured for filtering out the eddy current response located within region 164 to isolate the response signature generated by conductivity modifying agents 160. Alternatively, conductivity modifying agents 160 and these inherent variations may be used to collectively define the component identifier.

In addition, it may also be desirable to make locating identifying region 150 and conductivity modifying agents 160 more difficult, e.g., to avoid detection using conventional low-tech scanning means. Therefore, according to an exemplary embodiment, conductivity modifying agents 160 may be selected such that they are undetectable to the human eye or may require specialized scanning means to locate and interrogate conductivity modifying agents 160. For example, according to the illustrated embodiment, conductivity modifying agents 160 may have a color that matches the primary surface material or may be covered by a layer of primary material 162.

According to an exemplary embodiment of the present subject matter, it may be desirable to include one or more additional features on component 100 which assist the manufacturer or an end user in locating an identifying region 150 which may contain conductivity modifying agents 160. For example, as explained above, conductivity modifying agents 160 may not be visible to the human eye. Thus, to avoid the need to scan the entire surface 112 to locate and interrogate conductivity modifying agents 160, one or more datum features may be used as a reference from which an authorized end user may find identifying region 150.

More specifically, referring again to FIG. 1, component 100 further includes a datum feature 170 that is visible to the human eye or otherwise easily detectable. For example, according to the exemplary embodiment, datum feature 170 has a size that is greater than about one millimeter. Moreover, datum feature 170 may indicate both a position and an orientation of component 100. According to the illustrated embodiment, datum feature 170 is formed within surface 112 of component 100. However, it should be appreciated that according to alternative embodiments, datum feature 170 may be formed within the interior of component 100 or cross sectional layer 110 and/or within both the interior of cross sectional layer 110 and surface 112 of component.

Datum feature 170 is located at a predetermined location relative to identifying region 150—and thus conductivity modifying agents 160. In this manner, an authorized third party who knows the relative positioning of datum feature 170 and identifying region 150 may easily locate datum feature 170 and use it as a reference for locating and interrogating identifying region 150 to read the eddy current response signature generated by conductivity modifying agents 160. More specifically, an authenticating party may know where to position and how to orient eddy current probe 132 to read the component identifier.

It should be appreciated that component 100 is described herein only for the purpose of explaining aspects of the present subject matter. For example, component 100 will be used herein to describe exemplary methods of manufacturing and authenticating additively manufactured components. It should be appreciated that the additive manufacturing techniques discussed herein may be used to manufacture other components for use in any suitable device, for any suitable purpose, and in any suitable industry. Furthermore, the authentication methods described herein may be used to identify, authenticate, or otherwise distinguish such components. Thus, the exemplary components and methods described herein are used only to illustrate exemplary aspects of the present subject matter and are not intended to limit the scope of the present disclosure in any manner.

Now that the construction and configuration of component 100 according to an exemplary embodiment of the present subject matter has been presented, an exemplary method 200 for forming a component according to an exemplary embodiment of the present subject matter is provided. Method 200 can be used by a manufacturer to form component 100, or any other suitable part or component. It should be appreciated that the exemplary method 200 is discussed herein only to describe exemplary aspects of the present subject matter, and is not intended to be limiting.

Figure 5:
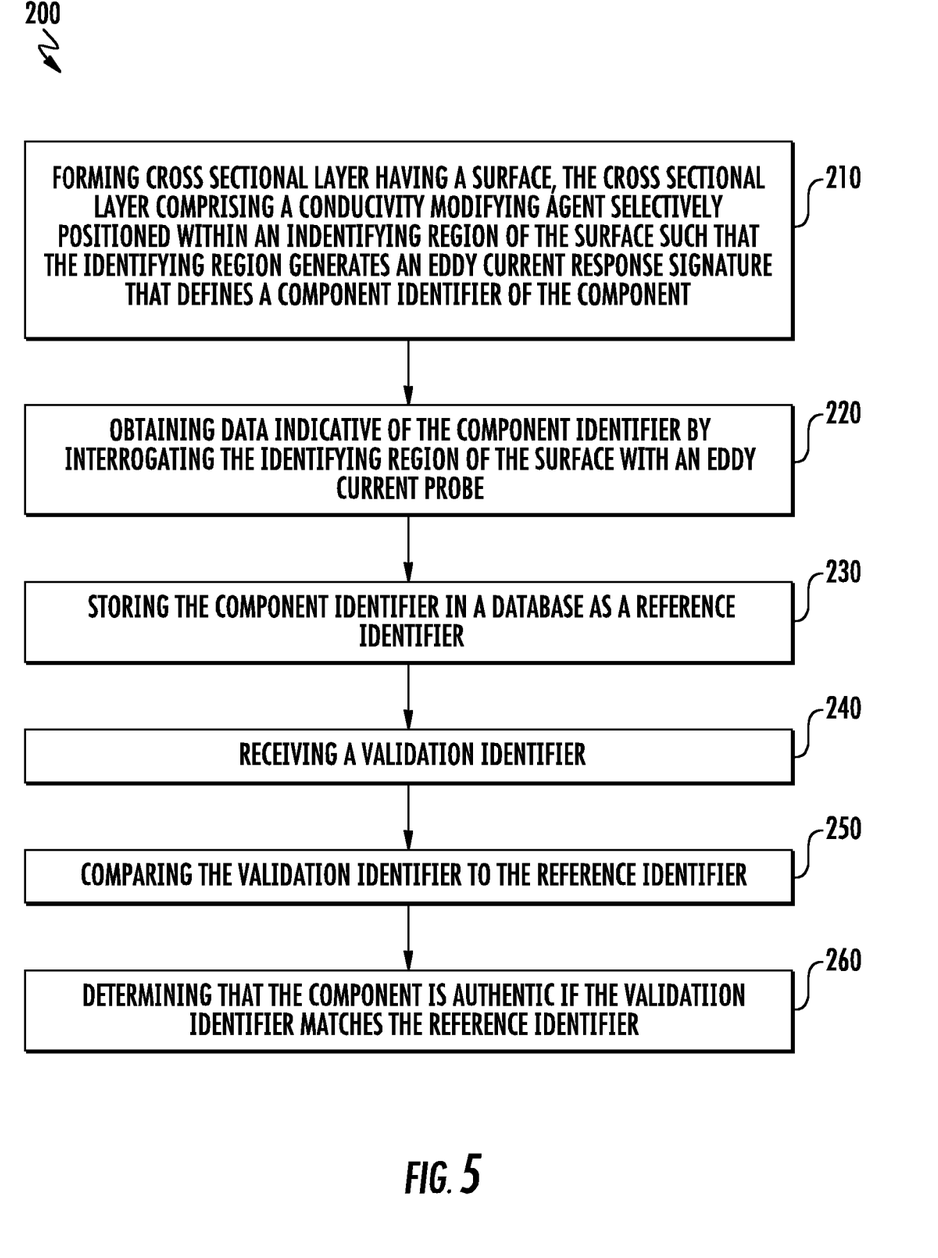
FIG. 5 is a method for manufacturing a component according to an exemplary embodiment of the present subject matter.

Referring now to FIG. 5, method 200 includes, at step 210, forming a cross sectional layer having a surface, the cross sectional layer including a conductivity modifying agent. This may include, for example, additively manufacturing a cross sectional layer and a surface, such as described above with respect to component 100. The surface may include a first material having a first conductivity and a second material having a second conductivity. According to exemplary embodiments, the second material is selectively positioned within an identifying region of the surface such that the identifying region generates an eddy current response signature that defines a component identifier of the component when interrogated by an eddy current probe.

As explained above, conductivity modifying agents 160 may be integrated into component 100 by selectively depositing material during an additive manufacturing process, through chemical vapor deposition, or using any other suitable method. According to exemplary embodiments, the surface further includes a datum feature which may be used to determine the specific position and orientation of the component. The datum feature may be useful in locating an identifying region and positioning an eddy current probe for interrogating the component, e.g., particularly when the conductivity modifying agents 160 are not readily detectable. Notably, according to alternative embodiments, step 210 may be omitted and steps 220 through 260 (described below) may be performed on any previously manufactured component for cataloguing a reference identifier for use in authentication.

Method 200 further includes, at step 220, obtaining data indicative of the component identifier by interrogating the identifying region of the surface with an eddy current probe. For example, step 220 may include interrogating identifying region 150 of surface 112 using eddy current probe 132 to generate a eddy current response signature similar to that illustrated in FIG. 4. The response signature may correspond to a unique component identifier that may be used for component authentication, as described further below.

Step 230 includes storing the component identifier in a database as a reference identifier. In this manner, the reference identifier stored in the database is associated with an authentic component. According to an exemplary embodiment, the manufacturer of the component enters the reference identifiers and controls the database of authentic components. According to the exemplary embodiments of FIG. 2, the database may be stored in controller 134, remote computing system 136, or both.

Thus, steps 210 through 230 may be generally used for querying or reading a component for identification data and storing that data for subsequent component validation, as described below with respect to steps 240 through 260. More specifically, a component is validated if it contains a component identifier that matches a reference identifier in the database. As used herein, the component identifier "matches" the reference identifier if a positive identification or verification may be made between the two parts. In this regard, a 100% identical match is not required, as the conductivity modifying agents may have degraded or changed during the life of the component, there may be variations in probe accuracy or calibration, etc. However, there should still be a sufficient resemblance between the component identifier and the reference identifier that a party may, with a reasonable degree of accuracy, determine that the component bearing the component identifier is indeed the same component from which the reference identifier was obtained and catalogued in the database.

Method 200 further includes, at step 240, receiving a validation identifier. As used in method 200, the validation identifier results from an interrogation of the identifying region of a component by a third party, such as an end user. Thus, if the component is authentic, the validation identifier is the component identifier which should match a reference identifier stored in the manufacturer's database. At step 250, the validation identifier is compared to the reference identifier (stored in the database), and step 260 includes determining that the component is authentic if the validation identifier matches the reference identifier. According to some embodiments, the authenticating party may further provide an indication that the component is authentic in response to determining that the component is authentic.

Figure 6:
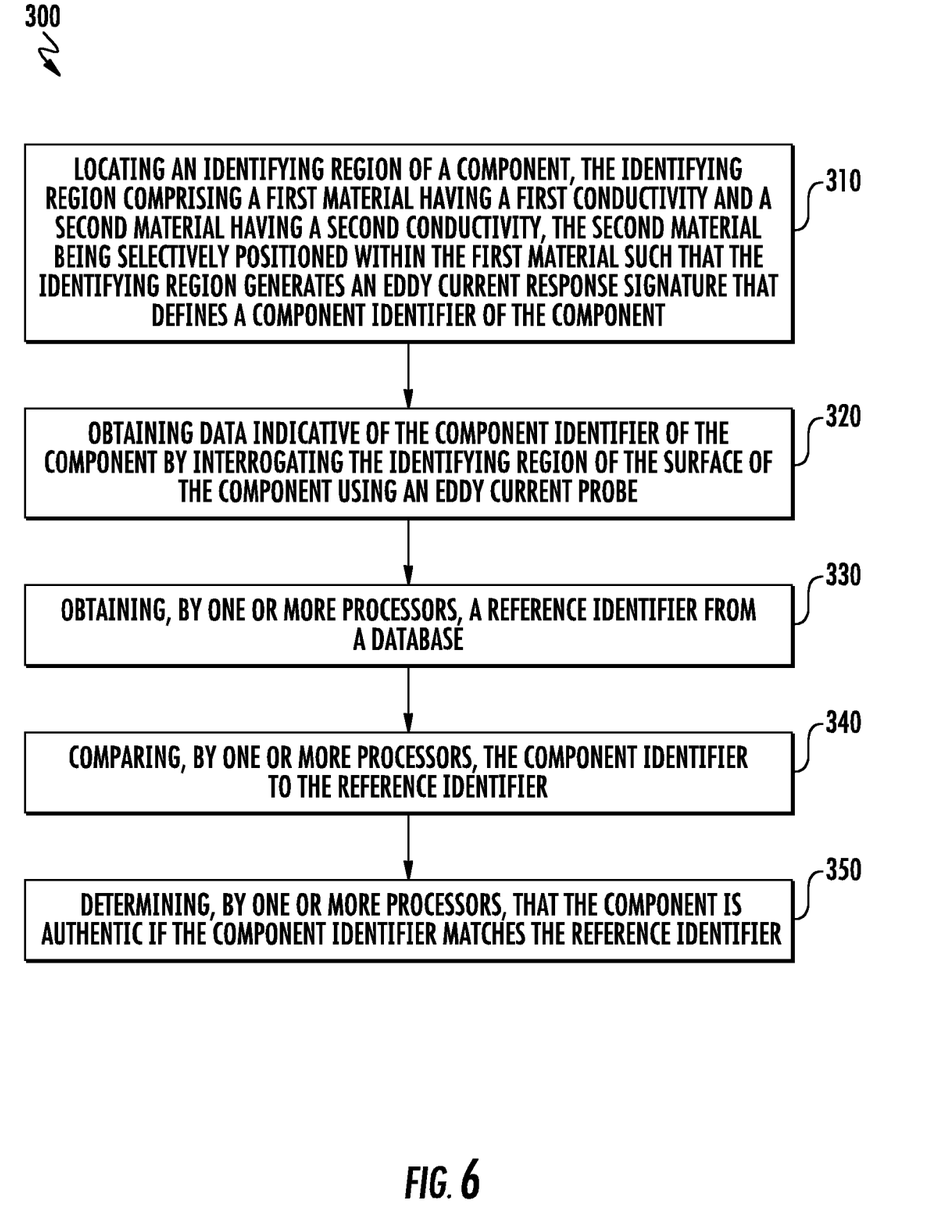
FIG. 6 is a method for authenticating a component according to an exemplary embodiment of the present subject matter.

Referring now to FIG. 6, an exemplary method 300 for authenticating a component according to an exemplary embodiment of the present subject matter is provided. Method 300 can be used by a customer or end user of a component, e.g., such as the end user of component 100, for validating that the component is authentic and is not a counterfeit component. It should be appreciated that the exemplary method 300 is discussed herein only to describe exemplary aspects of the present subject matter, and is not intended to be limiting.

Method 300 includes, at step 310, locating an identifying region of a component, the identifying region comprising a first material having a first conductivity and a second material having a second conductivity. As explained above, the second material is selectively positioned within the first material such that the identifying region generates an eddy current response signature that defines a component identifier of the component.

Step 320 includes obtaining data indicative of the component identifier of the component by interrogating the identifying region of the surface of the component using an eddy current probe. As explained above, the component includes conductivity modifying agents to generate an eddy current response signature that is unique to one or more components. According to exemplary embodiments, using component 100 as an example, identifying region 150 may be located by locating datum feature 170 and using knowledge of its relative position to locate this region.

Step 330 includes obtaining a reference identifier from a database. As explained in the description of method 200, the reference identifier may be the component identifier as measured and catalogued in the database by the manufacturer of the component. According to an exemplary embodiment, the reference identifier may be obtained from a database stored locally, e.g., on controller 134. Alternatively, the database may be remotely stored and may be accessed, for example, through remote computing system 136 via network 140.

Step 340 includes comparing the component identifier to the reference identifier and step 350 includes determining that the component is authentic if the component identifier matches the reference identifier. In this regard, for example, controller 134 may receive the reference identifier from a database and may be programmed to compare the reference identifier and the component identifier to positively determine whether the component is authentic. Alternatively, such a comparison can be performed remotely, e.g., by remote computing system 136.

As discussed herein, one or more portion(s) of methods 200 and 300 can be implemented by controller 134, by remote computing system 136, or both. Thus, for example, it should be appreciated that according to certain embodiments, the component authentication may be performed by a party other than the end user, e.g., the manufacturer. In such an embodiment, the end user may transmit the component identifier as measured from the component to the manufacturer. The manufacturer may then perform steps 330 through 350—i.e., obtain the reference identifier, compare the reference identifier and the component identifier, and make a determination regarding authenticity. If the component is determined to be authentic, the manufacturer may then transmit a signal to the end user indicating that the component is authentic. By contrast, if the component identifier does not match a reference identifier from the database, the manufacturer may provide an indication to the end user that the component might be a counterfeit.

FIGS. 5 and 6 depict steps performed in a particular order for purposes of illustration and discussion. Those of ordinary skill in the art, using the disclosures provided herein, will understand that the steps of any of the methods discussed herein can be adapted, rearranged, expanded, omitted, or modified in various ways without deviating from the scope of the present disclosure. Moreover, although aspects of methods 200, 300 are explained using component 100 as an example, it should be appreciated that these methods may be applied to authenticate any suitable component.

An additively manufactured component and a method for manufacturing and authenticating that component are described above. Using the additive manufacturing methods described herein, the component may include identifying features that are smaller, more complex, and more intricate than possible using prior manufacturing methods. In addition, these features may be difficult or impossible to detect, very difficult to reverse engineer, and nearly impossible reproduce, e.g., for the purpose of producing counterfeit products. For example, the conductivity modifying agents may be designed to appear random and non-obvious. These features may further be formed such that they are not visible to the human eye and may be read using eddy current interrogation methods directed to a specific identifying region of the component that is unknown to third parties. These features may be introduced during the design of the component, such that they may be easily integrated into components during the build process at little or no additional cost. The features may also serve as a robust identifier capable of withstanding high temperatures without degradation throughout the life of the component, with little or no impact on the quality of the component. Furthermore, these features may be authenticated through comparison with previously catalogued reference identifiers.

Figure 7:
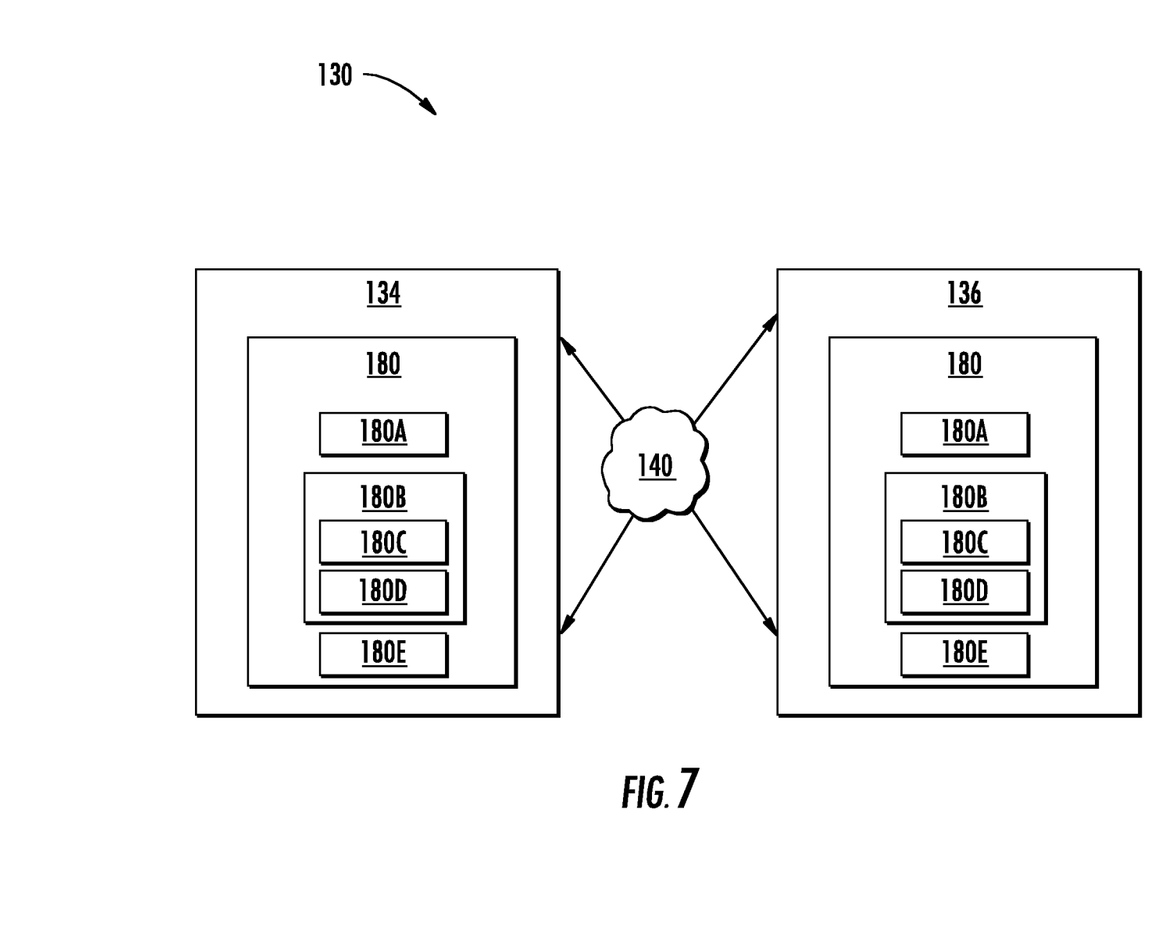
FIG. 7 depicts certain components of an authentication system according to example embodiments of the present subject matter.

FIG. 7 depicts authentication system 130 according to example embodiments of the present disclosure. As described above, authentication system 130 can include one or more controllers 134 and/or remote computing systems 136, which can be configured to communicate via one or more network(s) (e.g., network(s) 140). According to the illustrated embodiment, remote computing system 136 is remote from controller 134. However, it should be appreciated that according to alternative embodiments, remote computing system 136 can be included with or otherwise embodied by controller 134.

Controller 134 and remote computing system 136 can include one or more computing device(s) 180. Although similar reference numerals will be used herein for describing the computing device(s) 180 associated with controller 134 and remote computing system 136, respectively, it should be appreciated that each of controller 134 and remote computing system 136 may have a dedicated computing device 180 not shared with the other. According to still another embodiment, only a single computing device 180 may be used to implement methods 200 and 300 as described above, and that computing device 180 may be included as part of controller 134 or remote computing system 136.

Computing device(s) 180 can include one or more processor(s) 180A and one or more memory device(s) 180B. The one or more processor(s) 180A can include any suitable processing device, such as a microprocessor, microcontroller, integrated circuit, an application specific integrated circuit (ASIC), a digital signal processor (DSP), a field-programmable gate array (FPGA), logic device, one or more central processing units (CPUs), graphics processing units (GPUs) (e.g., dedicated to efficiently rendering images), processing units performing other specialized calculations, etc. The memory device(s) 180B can include one or more non-transitory computer-readable storage medium(s), such as RAM, ROM, EEPROM, EPROM, flash memory devices, magnetic disks, etc., and/or combinations thereof.

The memory device(s) 180B can include one or more computer-readable media and can store information accessible by the one or more processor(s) 180A, including instructions 180C that can be executed by the one or more processor(s) 180A. For instance, the memory device(s) 180B can store instructions 180C for running one or more software applications, displaying a user interface, receiving user input, processing user input, etc. In some implementations, the instructions 180C can be executed by the one or more processor(s) 180A to cause the one or more processor(s) 180A to perform operations, as described herein (e.g., one or more portions of methods 200, 300). More specifically, for example, the instructions 180C may be executed to perform a comparison between a reference identifier and a component identifier, to perform an authentication analysis, to transmit an indication of authenticity, etc. The instructions 180C can be software written in any suitable programming language or can be implemented in hardware. Additionally, and/or alternatively, the instructions 180C can be executed in logically and/or virtually separate threads on processor(s) 180A.

The one or more memory device(s) 180B can also store data 180D that can be retrieved, manipulated, created, or stored by the one or more processor(s) 180A. The data 180D can include, for instance, data indicative of reference identifiers associated with authentic additively manufactured components. The data 180D can be stored in one or more database(s). The one or more database(s) can be connected to controller 134 and/or remote computing system 136 by a high bandwidth LAN or WAN, or can also be connected to controller through network(s) 140. The one or more database(s) can be split up so that they are located in multiple locales. In some implementations, the data 180D can be received from another device.

The computing device(s) 180 can also include a communication interface 180E used to communicate with one or more other component(s) of authentication system 130 (e.g., controller 134 or remote computing system 136) over the network(s) 140. The communication interface 180E can include any suitable components for interfacing with one or more network(s), including for example, transmitters, receivers, ports, controllers, antennas, or other suitable components.

The network(s) 140 can be any type of communications network, such as a local area network (e.g. intranet), wide area network (e.g. Internet), cellular network, or some combination thereof and can include any number of wired and/or wireless links. The network(s) 140 can also include a direct connection between one or more component(s) of authentication system 130. In general, communication over the network(s) 140 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

The technology discussed herein makes reference to servers, databases, software applications, and other computer-based systems, as well as actions taken and information sent to and from such systems. It should be appreciated that the inherent flexibility of computer-based systems allows for a great variety of possible configurations, combinations, and divisions of tasks and functionality between and among components. For instance, computer processes discussed herein can be implemented using a single computing device or multiple computing devices (e.g., servers) working in combination. Databases and applications can be implemented on a single system or distributed across multiple systems. Distributed components can operate sequentially or in parallel. Furthermore, computing tasks discussed herein as being performed at the computing system (e.g., a server system) can instead be performed at a user computing device. Likewise, computing tasks discussed herein as being performed at the user computing device can instead be performed at the computing system.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for manufacturing a component comprising:
    forming a cross sectional layer having a surface defining a visible datum feature indicating a position and an orientation of the component, the cross sectional layer comprising a conductivity modifying agent;
    obtaining data indicative of a component identifier by interrogating an identifying region of the surface with an eddy current probe, wherein the conductivity modifying agent is selectively positioned within the identifying region of the surface such that the interrogation of the identifying region results in an eddy current response signature that defines the component identifier of the component; and
    storing the component identifier in a database as a reference identifier.

2. The method of claim 1, further comprising:
    forming the datum feature on the component at a predetermined location relative to the identifying region.

3. The method of claim 1, wherein the conductivity modifying agent is selectively deposited on the identifying region of the cross sectional layer, the method further comprising:
    directing energy from an energy source onto the conductivity modifying agent to fuse the conductivity modifying agent to the cross sectional layer.

4. The method of claim 1, wherein the conductivity modifying agent is deposited using chemical vapor deposition.

5. The method of claim 1, wherein the conductivity modifying agent is a first conductivity modifying agent, the identifying region of the surface comprising a second conductivity modifying agent having a conductivity different than the first conductivity modifying agent.

6. The method of claim 1, wherein forming the surface on the cross sectional layer comprises:
    depositing a layer of additive material, the layer of additive material comprising the conductivity modifying agent selectively positioned within the layer of additive material; and
    directing energy from an energy source onto the layer of additive material to fuse at least a portion of the conductivity modifying agent to the cross sectional layer.

7. The method of claim 1, further comprising:
    receiving a validation identifier;
    comparing the validation identifier to the reference identifier; and
    determining that the component is authentic if the validation identifier matches the reference identifier.

8. The method of claim 1, wherein the eddy current probe comprises an array of two or more induction coils.

9. The method of claim 1, wherein interrogating the identifying region with the eddy current probe comprises interrogating the identifying region using at least two different frequencies.

10. A method of authenticating a component, the method comprising:
    locating a visible datum feature on the component, the datum feature being positioned at a predetermined location and orientation relative to the identifying region; and
    determining, by one or more processors, the location of the identifying region based on the location of the datum feature, the identifying region comprising a first material having a first conductivity and a second material having a second conductivity;
    obtaining data indicative of the component identifier of the component by interrogating the identifying region of the surface of the component using an eddy current probe, the second material being selectively positioned within the first material such that the interrogation of the identifying region results in an eddy current response signature that defines a component identifier of the component; and
    determining, by one or more processors, that the component is authentic based on the data acquired by the eddy current probe.

11. The method of claim 10, wherein determining that the component is authentic comprises:
    obtaining, by one or more processors, a reference identifier from a database;
    comparing, by one or more processors, the component identifier to the reference identifier; and
    determining, by one or more processors, that the component is authentic if the component identifier matches the reference identifier.

12. The method of claim 10, wherein the second material is additively manufactured onto the component or deposited using chemical vapor deposition.

13. The method of claim 10, wherein the identifying region comprises a third material having a third conductivity.

14. The method of claim 10, wherein the eddy current probe comprises an array of two or more induction coils.

15. The method of claim 10, wherein interrogating the identifying region with the eddy current probe comprises interrogating the identifying region using at least two different frequencies.

16. A system for authenticating an additively manufactured component, the system comprising:
    one or more processors; and
    one or more memory devices, the one or more memory devices storing computer-readable instructions that when executed by the one or more processors cause the one or more processors to perform operations, the operations comprising:
        locating a visible datum feature on the component, the datum feature being positioned at a predetermined location and orientation relative to an identifying region; and
        determining, by one or more processors, the location of the identifying region based on the location of the datum feature, the identifying region comprising a first material having a first conductivity and a second material having a second conductivity;
        determining the component identifier by interrogating the identifying region of the component using an eddy current probe, the second material being selectively positioned within the first material such that the interrogation of the identifying region results in an eddy current response signature that defines a component identifier of the component;

obtaining a reference identifier from a database; and determining that the component is authentic if the component identifier matches the reference identifier.

17. The system of claim 16, wherein the second material is additively manufactured onto the component or deposited using chemical vapor deposition.

18. The system of claim 16, wherein the eddy current probe comprises an array of two or more induction coils and wherein interrogating the identifying region with the eddy current probe comprises interrogating the identifying region using at least two different frequencies.

* * * * *